US011995161B2

(12) United States Patent
Humborstad et al.

(10) Patent No.: US 11,995,161 B2
(45) Date of Patent: May 28, 2024

(54) BIOMETRIC ENROLMENT

(71) Applicant: ZWIPE AS, Oslo (NO)

(72) Inventors: Kim Kristian Humborstad, Oslo (NO); Kristian Trengereid, Oslo (NO)

(73) Assignee: ZWIPE AS, Oslo (NO)

(*) Notice: Subject to any disclaimer, the term of this patent is extended or adjusted under 35 U.S.C. 154(b) by 628 days.

(21) Appl. No.: 17/057,893

(22) PCT Filed: Jun. 28, 2019

(86) PCT No.: PCT/EP2019/067473
§ 371 (c)(1),
(2) Date: Nov. 23, 2020

(87) PCT Pub. No.: WO2020/002678
PCT Pub. Date: Jan. 2, 2020

(65) Prior Publication Data
US 2021/0374218 A1 Dec. 2, 2021

(30) Foreign Application Priority Data

Jun. 28, 2018 (GB) .................................. 1810658

(51) Int. Cl.
G06F 21/32 (2013.01)
A61B 5/117 (2016.01)
G07B 17/00 (2006.01)

(52) U.S. Cl.
CPC .............. *G06F 21/32* (2013.01); *A61B 5/117* (2013.01); *G07B 17/00733* (2013.01); *G07B 2017/00838* (2013.01)

(58) Field of Classification Search
CPC ........ G06Q 20/40145; G07B 16/00733; G06B 2017/00838; A61B 5/117; G06F 21/32
See application file for complete search history.

(56) References Cited

U.S. PATENT DOCUMENTS 5,728,998 A 3/1998 Novis et al.
6,990,588 B1* 1/2006 Yasukura ............... G07C 9/257
713/161

(Continued)

FOREIGN PATENT DOCUMENTS

BE 904058 A 5/1986
CN 1169001 A 12/1997

(Continued)

OTHER PUBLICATIONS

Taiwanese Office Action, PA512-230531 (13 pp.).

(Continued)

*Primary Examiner* — Shin-Hon (Eric) Chen
*Assistant Examiner* — Thomas A Carnes
(74) *Attorney, Agent, or Firm* — Eversheds Sutherland (US) LLP

(57) ABSTRACT

A method is described for biometric enrolment of a biometrically authorisable device having a biometric sensor for identification of an authorised user and a processor capable of permitting access to one or more secure feature(s) based on authentication of the user's identity. The enrolment method includes mounting the biometrically authorisable device to a holder in order to form an enrolment system arranged to be delivered to the end user by mail. The holder has a power source such that during delivery the supply of power is deactivated and the holder includes a switching arrangement configured to activate the supply of power in response to manipulation of the holder. The enrolment system is delivered to the user and the supply of power is activated in response to manipulation of the holder by the user.

21 Claims, 5 Drawing Sheets

(56) References Cited

U.S. PATENT DOCUMENTS

| | | | |
|---|---|---|---|
| 7,441,709 B2 | 10/2008 | Chan et al. | |
| 7,679,005 B2 | 3/2010 | Chan et al. | |
| 7,721,954 B1 | 5/2010 | Karamian et al. | |
| 8,181,879 B2 | 5/2012 | Landau et al. | |
| 9,607,189 B2* | 3/2017 | Gardiner | G06Q 20/353 |
| 10,176,415 B2* | 1/2019 | Wendling | G06K 19/07354 |
| 2004/0188520 A1* | 9/2004 | Kohta | G06Q 20/342 |
| | | | 235/382 |
| 2005/0122209 A1* | 6/2005 | Black | G06Q 20/4014 |
| | | | 340/5.4 |
| 2005/0139685 A1* | 6/2005 | Kozlay | G06K 19/07354 |
| | | | 235/492 |
| 2006/0000894 A1* | 1/2006 | Bonalle | G06K 19/0718 |
| | | | 235/382 |
| 2006/0213973 A1 | 9/2006 | Chan et al. | |
| 2006/0214010 A1 | 9/2006 | Chan et al. | |
| 2007/0187487 A1 | 8/2007 | Wilen | |
| 2008/0109309 A1 | 5/2008 | Landau et al. | |
| 2008/0156690 A1 | 7/2008 | Landau et al. | |
| 2009/0014542 A1 | 1/2009 | Gelbman | |
| 2009/0095810 A1* | 4/2009 | Cannon | G06F 21/32 |
| | | | 235/380 |
| 2009/0134223 A1 | 5/2009 | Matthews et al. | |
| 2011/0240728 A9* | 10/2011 | Arnouse | H04N 21/4143 |
| | | | 235/487 |
| 2013/0129162 A1* | 5/2013 | Cheng | G06V 40/20 |
| | | | 382/124 |
| 2013/0254533 A1* | 9/2013 | Welch | G06F 21/32 |
| | | | 713/155 |
| 2015/0310440 A1 | 10/2015 | Hynes et al. | |
| 2016/0203346 A1* | 7/2016 | Gardiner | G06K 19/0718 |
| | | | 235/380 |
| 2016/0300236 A1 | 10/2016 | Wiley et al. | |
| 2016/0371528 A1* | 12/2016 | Slaby | G06V 40/1394 |
| 2017/0300680 A1 | 10/2017 | Wendling | |
| 2018/0268274 A1 | 9/2018 | Lowe | |
| 2018/0276519 A1* | 9/2018 | Benkley, III | G06F 21/45 |
| 2018/0330216 A1 | 11/2018 | Wendling | |
| 2019/0065918 A1* | 2/2019 | Humborstad | G06K 19/0718 |
| 2019/0213578 A1 | 7/2019 | Reijkens | |
| 2019/0220582 A1* | 7/2019 | Humborstad | G06F 21/32 |
| 2020/0005304 A1* | 1/2020 | Almers | G06Q 20/40145 |
| 2021/0042759 A1* | 2/2021 | Larsen | G06Q 20/4012 |
| 2021/0184857 A1* | 6/2021 | Chen | H04L 63/0861 |
| 2021/0374218 A1* | 12/2021 | Humborstad | G06K 19/0718 |

FOREIGN PATENT DOCUMENTS

| | | | | |
|---|---|---|---|---|
| CN | 1148692 C | 5/2004 | | |
| CN | 2735452 Y | 10/2005 | | |
| CN | 104720241 A | 6/2015 | | |
| CN | 205354077 A | 6/2016 | | |
| CN | 205354077 U | 6/2016 | | |
| CN | 106203593 A | 12/2016 | | |
| CN | 206611477 U | 11/2017 | | |
| DE | 19634876 A1 | 3/1998 | | |
| DE | 19713711 A1 | 4/1998 | | |
| DE | 69703461 T2 | 6/2001 | | |
| EP | 0802501 A1 | 10/1997 | | |
| EP | 1441306 A1 * | 7/2004 | | G06K 19/0701 |
| EP | 3382599 A2 | 10/2018 | | |
| FR | 2713058 A1 | 6/1995 | | |
| JP | H02-81291 A | 3/1990 | | |
| JP | 10040348 A2 | 2/1998 | | |
| JP | 2006-189997 A | 7/2006 | | |
| KR | 19970066983 A | 10/1997 | | |
| TW | 279307 B | 10/1987 | | |
| TW | 201901512 A | 1/2019 | | |
| WO | 2002065268 A1 | 8/2002 | | |
| WO | 08082617 A2 | 7/2008 | | |
| WO | 2017/149015 A1 | 9/2017 | | |

OTHER PUBLICATIONS

International Search Report and Written Opinion, PCT/EP2019/067473, dated Oct. 11, 2019 (15 pp.).

Search Report for GB1810658.3, dated Dec. 17, 2018 (3 pp.).

Office Action for JP2020-572937, dated May 2, 2203 (with English Translation) (10 pp.).

Fitzgerald, Kate, "Mastercard debuts DIY fingerprint kit for biometric cards", The Latest, PaymentSources, https://www.paymentssource.com/news/mastercard-debuts-diy-fingerprint-kit-for-biometric-cards; dated Feb. 2018 (4 pp.).

* cited by examiner

BIOMETRIC ENROLMENT

The present invention relates to method for biometric enrolment of a biometrically authorisable device having one or more secure feature(s), as well as to a corresponding biometric enrolment system.

Biometrically authorisable devices such as smartcards are becoming increasingly more widely used and include, for example access cards, credit cards, debit cards, pre-pay cards, loyalty cards, identity cards, and so on. Smartcards are electronic cards with the ability to store data and to interact with the user and/or with outside devices, for example via contactless technologies such as RFID. These cards can interact with readers to communicate information in order to enable access, to authorise transactions and so on. Other biometrically authorisable devices include wearables such as smart watches, security tokens, dongles and so on.

Biometric authorisation such as fingerprint authorisation is becoming increasingly more widely used. Smartcards with biometric authorisation can interact with the user via sensors in order to enable access to secure features of the smartcard, for example in order to authorise financial transactions. Other biometrically authorised devices include Challenges arise for biometrically authorisable devices such as smartcards in relation to the constraints from the size of the device, the available power resource, and the required functionality. For a smartcard the size of the device may be limited by ISO standards for credit cards in the case of a smartcard operable as a payment card. Thus, all components must fit into a tightly packaged form, as well as ideally being flexible and lightweight.

The power that is available is constrained by the size of the device and the power source that is selected. A wired connection to an external power source could be included, such as power drawn via a connection with the contacts of a 'chip and pin' type smartcard. However there are technical constraints from the external power source in relation to the current drawn via this approach as well as difficulties in handling a large power at the smartcard itself. A wireless connection may be used with power being harvested using an antenna at the device and a contactless coupling with an external antenna, such as an antenna of a smartcard reader. Prior art proposals for implementations of this are described in WO 2016/055663 and in WO 2017/025481. It will be understood that there are significant advantages to the use of harvested power, but there can be compromises in view of limitations on the amount of power that can be obtained in this way.

It is known that enrolment of biometric data provides particular challenges for smaller devices such as smartcards, especially in the case where harvested power is used, i.e. where there may not be any significant amount of power stored on the smartcard via a battery or the like. In an earlier application, published as WO 2016/055661, the applicant described, inter alia, a method in which an enrolment mode is enabled with the smartcard in use at an RFID terminal (for example an ATM for a bank card), where the enrolment mode is protected with an authorisation code sent separately from the smartcard. With this example from WO 2016/055661 whilst the smartcard is receiving power from the RFID terminal then the user can enroll their biometric (e.g. a fingerprint) via a biometric sensor integrated into the smartcard.

It is desirable to use the biometric sensor integrated in the smartcard during enrolment. This avoids the need for potentially insecure transmission of the biometric data over a network, and instead the biometric data can be securely kept on the smartcard with no requirement for external storage or transmission. It also increases the accuracy of the biometric identification process since the exact same sensor is used for enrolment as is used for later authentication by checking the user's biometric against a stored biometric. However, whilst the proposals in WO 2016/055661 provided a significant advance in the art there remains a need for alternative enrolment systems for biometrically authorisable devices such as smartcards.

Viewed from a first aspect the present invention provides a method for biometric enrolment of a biometrically authorisable device, wherein the biometrically authorisable device comprises a biometric sensor for identification of an authorised user and a processor capable of permitting access to one or more secure feature(s) of the biometrically authorisable device based on authentication of the user's identity via the biometric sensor, and wherein the method comprises:

mounting the biometrically authorisable device to a holder in order to form an enrolment system, wherein the enrolment system including the biometrically authorisable device and the holder is arranged to be delivered to the end user by a mail delivery service;

providing the holder with a power source capable of supplying power to the biometrically authorisable device, wherein the holder is arranged such that during the delivery of the enrolment system the supply of power from the power source to the biometrically authorisable device is deactivated, and the holder includes a switching arrangement configured to activate the supply of power from the power source to the biometrically authorisable device in response to manipulation of the holder by a user after delivery of the enrolment system;

delivering the enrolment system to an end user;

activating the supply of power from the power source in the holder to the biometrically authorisable device in response to manipulation of the holder by the user;

enabling an enrolment mode of the biometrically authorisable device in which the user's biometric data can be enrolled to the biometrically authorisable device via an enrolment process using the biometric sensor of the biometrically authorisable device; and using the power from the power source to power the biometrically authorisable device during the enrolment process.

By providing the biometrically authorisable device along with a holder in an enrolment system that can be delivered to the user in a single delivery then the enrolment process is significantly simplified. The enrolment system may be self-contained in that it will enable enrolment of biometric data without the need for interaction with any external system or network. The biometrically authorisable device has access to power from the holder and therefore even in the case of a biometrically authorisable device with no internal power source the user can perform the enrolment process at the point of delivery and does not need to transport the biometrically authorisable device to a separate reader or enrolment system, or pair the device up with a power source available to the user from elsewhere. Advantageously the biometrically authorisable device can have no internal power source and hence may rely on power from an external source including harvested power, such as power obtained via an antenna as described in WO 2016/055663 or in WO 2017/025481.

In the case of a smartcard (e.g. a payment card) as the biometrically authorisable device then the enrolment process experienced by the user fits neatly within conventional card activation procedures since the user is provided with all of the necessary features in the package when the smartcard is delivered to enroll via power from the holder in the user's home or workplace. If a suitable system is provided for activation of the secure features of the smartcard then the user might be able to immediately use the biometrically protected smartcard, such as biometrically secured contactless payments for a payment card. The enrolment system and the holder can be arranged for intuitive activation of the power supply from the power source in the holder to the biometrically authorisable device. For example, as discussed below the manipulation of the holder by the user may include an action normally done upon receipt of a delivery, such as opening a package or opening a 'gift card' type holder. Thus, the power source for the enrolment process can be similar to known deliverable power sources such as the batteries used for "singing gift cards" and the like. Thus, the enrolment system may optionally use battery technology that has already been proven for safe use within mail delivery services, which avoids regulatory issues that might otherwise arise.

The reference to mail delivery should be understood to include any suitable system for delivery of physical items, such as postal services, courier services and so on. The holder and the biometrically authorisable device may be housed within a suitable outer package to protect it during the delivery to the user. In the case of a biometrically authorisable device with a flat shape, such as a smartcard, then the package may be an envelope and hence would be readily delivered to the user by all mail delivery systems that can deliver letters and similar items.

The holder may be a folded card, and the folded card may be configured to be unfolded by a user in order to reveal the smartcard and enrolment system (i.e. a biometric sensor). Alternatively, the holder may comprise a box that contains a slider, similar to a pill box or the like. If the holder comprises a box, it may further comprise a tab which when pulled by a user, reveals the smartcard and/or enrolment system from inside of the box. The smartcard and/or enrolment system may be attached to the slider and the slider may be configured to appear from inside of the box (e.g. by sliding out of an opening of the box) when the tab is pulled. Whilst the holder may take any of the above described configurations, the skilled person will appreciate that the holder may comprise any system that is suitable for mail delivery and configured to hold the smartcard and enrolment system during transit. The step of manipulation of the holder by the user results in activation of the power supply via the switching arrangement. This may include a physical switch for completing an electrical circuit. As noted above, the holder may be similar to so-called "singing gift cards" and may use a switching arrangement known from such devices, in which case the manipulation of the holder may include opening a folded card. Other manipulations may be used, such as pulling a tab or pressing a button. In some cases it will be appreciated that the manipulation may be a natural movement that the user will carry out, such as opening a folded card. Where the holder comprises a box with a slider then the step of manipulation of the holder by the user may include sliding the card out of the box and/or pulling the tab. The holder may include printed instructions to the user to prompt the user to carry out the required manipulation. For example, written or diagrammatic instructions may be included on the holder. The holder may also provide the user with instructions for how to carry out the biometric enrolment following activation of the power supply from the power source. For example, these instructions may be written or diagrammatic instructions printed on the holder and/or the holder may include a powered interface for providing instructions, such as a speaker for providing audible instructions or a graphical user interface for providing visible instructions.

As will be appreciated from the discussion above, advantageous implementations for the enrolment method use it for biometric enrolment of smartcards, such as payment cards or access cards, especially smartcards with no internal power storage, such as smartcards using harvested power. The smartcard may be any one of: an access card, a credit card, a debit card, a pre-pay card, a loyalty card, an identity card, a transport card or the like. The smartcard optionally has a width of between 85.47 mm and 85.72 mm, and a height of between 53.92 mm and 54.03 mm. The smartcard may have a thickness less than 0.84 mm, and optionally of about 0.76 mm (e.g. ±0.08 mm). More generally, the smartcard may comply with ISO 7816, which is the specification for a smartcard.

Other biometrically authorisable devices may also use the enrolment method, such as wearables and devices used in the context of interactions via the Internet of Things, especially small portable devices. An example of a wearable biometrically authorisable device is a smart watch. This might be the biometrically authorisable device in an embodiment of the invention where the holder supplies power to the watch during an enrolment process upon first delivery of the watch to a user, such as after an online purchase. In one example the holder is a watch box and opening the box activates the power supply.

The biometrically authorisable device may be capable of wireless communication, such as using RFID or NFC communication. Alternatively or additionally the biometrically authorisable device may comprise a contact connection, for example via a contact pad or the like such as those used for "chip and pin" cards. In various embodiments, the biometrically authorisable device may permit both wireless communication and contact communication. It will be appreciated that the biometrically authorisable device may have electrical contacts for receiving power from the power source on the holder, and in that case the electrical contacts for receiving power may also act as contact connections for communication purposes.

The biometric sensor may be a fingerprint sensor, which is preferably embedded into the biometrically authorisable device. With this feature the authorised user may initially enroll their fingerprint onto the biometrically authorisable device, and may then be required to place their finger or thumb on the fingerprint sensor in order to authorise some or all uses of the biometrically authorisable device. A fingerprint matching algorithm on the processor may be used to identify a fingerprint match between an enrolled user and a fingerprint sensed by the fingerprint sensor.

The step of enabling an enrolment mode of the biometrically authorisable device may be carried out upon activation of the power supply without any added step. Thus, biometric enrolment may be permitted automatically after a simple physical manipulation of the holder and without added authentication of the user. In this case the biometrically authorisable device may require a later authorisation step via an external system after biometric enrolment and before activation of some or all of the secure feature(s) of the device, such as payment functions for a payment smartcard. Possible later authorisation steps via an external system are discussed below. This approach has advantages in terms of simplification of the enrolment system and keeping the enrolment method aligned with existing activation processes, such as activation of payment cards received by mail. Alternatively, the enrolment system may require added authentication to confirm the identity of the user before the enrolment mode is enabled. The method could include the use of both of added authentication by the enrolment system as well as a later authorisation step via an external system.

In the case where the enrolment system requires added authentication to confirm the identity of the user before the enrolment mode is enabled then this may make use of an interface on the holder and/or of an interface on the biometrically authorisable device.

The interface on the biometrically authorisable device may be the biometric sensor. As has been described by the applicant in WO 2017/149015 and WO 2018/087336 there are various possibilities for interaction with a biometric sensor as a secondary identification system, in particular when a fingerprint sensor is present and can be used to detect a non-fingerprint interaction with the biometrically authorisable device. In this case the user may be provided with a suitable instruction defining a pattern or sequence of actions that the fingerprint sensor (or other biometric sensor) can detect in order to confirm that the user is authorised. Further details of this are set out below. Such an instruction may be delivered to the user separately to the enrolment system, such as in a separate mail delivery in the same way that a PIN is sent separately from a payment card.

Another possibility is for an interface to be included on the holder, such as a PIN pad or other interface allowing a code to be entered. Once again there may be a separate delivery of details of the code, such as via a separate mail delivery. The user can enter the code in order to active the enrolment mode of the biometrically authorisable device. Optionally this may also activate access to some or all of the secure feature(s) of the device, such as payment functions for a payment smartcard.

If the method includes a later authorisation step via an external system before activation of some or all of the secure feature(s) of the biometrically authorisable device then this may be done by various methods, including methods known for activation of conventional payment cards. It is advantageous to use this approach since it is seen as beneficial to simplify the enrolment system and the enrolment steps for the user by allowing biometric enrolment automatically after a simple physical manipulation of the holder and without added authentication of the user. In this case the activation of the secure feature(s) of the biometrically authorisable device may be possible via a later authorisation step using one or more of:

An online system such as online banking for a payment card, in which case the activation may require the user to:
  Log on to Online banking
  Select the account to activate the card for
  Click on 'Activate new card' and follow the instructions.
An app, such as a smartphone or PC application that may be provided by the issuer of the biometrically authorisable device:
  The user opens a secure app to confirm enrolment and the intention to utilize the secure feature(s), which are activated after authentication according to the security features of the app.
Telephone call, such as via calling the issuer of the biometrically authorisable device (e.g. a bank for a payment card) and by providing appropriate personal details to confirm the user's identity.

For a payment smartcard, using the card at an ATM or point of sale:
  The user makes a transaction using the PIN code (such as a cash withdrawal, balance enquiry or mobile top-up) and the smartcard will be automatically activated with future use of the smartcard linked to the PIN and/or biometric authentication as required by the user and/or the issuer of the card.

The interaction between the holder and the biometrically authorisable device may involve physical mounting of the biometrically authorisable device to the holder, such as mounting within a suitable recess. The mounting of the biometrically authorisable device to the holder may include an electrical connection for forming an electrical circuit with the biometrically authorisable device and the power source of the holder. Thus, the biometrically authorisable device should not need to be moved or reconfigured relative to the holder in order to activate the supply of power. Instead the required electrical connection should already be in place when the enrolment system is delivered to the user, with activation of the power supply being reliant on manipulation of the holder without relative movement of the holder and the biometrically authorisable device. In one example the biometrically authorisable device is held on the holder in a recess with a tab extending over the biometrically authorisable device to provide an electrical connection to a contact point on the biometrically authorisable device. Where the biometrically authorisable device is a smartcard then the contact point may be a "chip and pin" contact pad.

The interaction between the holder and the biometrically authorisable device may be limited to the supply of power, such that the holder can include a simple power supply circuit that has a switching function via the switching arrangement and has no other function. Alternatively the holder may itself be a 'smart' device and there may be communication of data between the holder and the biometrically authorisable device in addition to power. Data may be transferred between the holder and the biometrically authorisable device via wired or wireless communication protocols. In the case of wired communication of data this may use the same electrical connections as the power supply. As noted above, the biometrically authorisable device may comprise a contact connection, for example via a contact pad or the like such as those used for "chip and pin" smartcards, and this contact pad may be used for both a power supply from the holder to the biometrically authorisable device and for communication of data. In the case of wireless communication of data this may use a wireless communication system provided on the biometrically authorisable device for other purposes, such as an RFID communication interface provided for RFID communications during normal use of the biometrically authorisable device. Where the biometrically authorisable device is a smartcard then an RFID antenna is often included, such as for contactless communication for a payment smartcard or a transport system smartcard.

Where the biometrically authorisable device and the holder are in communication with each other for transfer of data then the holder may include a processor controlling the data transfer and/or controlling operations of the holder in reaction to data transfer. The holder may provide the biometrically authorisable device with an unlock signal in the case of added authentication via PIN entry or the like on the holder. The holder and the biometrically authorisable device may use public key interchange for added security. The holder may prompt certain modes of operation of the biometrically authorisable device in conjunction with the enrolment mode, such as causing LEDs to light up or causing a display on the biometrically authorisable device to show certain information to the user. In the latter case the biometrically authorisable device may include a GUI such as an LED or LCD display or the like.

Viewed from a second aspect, the invention provides an enrolment system for biometric enrolment of a biometrically authorisable device, the enrolment system comprising the biometrically authorisable device and a holder for the biometrically authorisable device, wherein the biometrically authorisable device is mounted to the holder, and wherein the enrolment system including the biometrically authorisable device and the holder is arranged to be delivered to an end user by a mail delivery service;

wherein the biometrically authorisable device comprises a biometric sensor for identification of an authorised user and a processor capable of permitting access to one or more secure feature(s) of the biometrically authorisable device based on authentication of the user's identity via the biometric sensor;

wherein the holder includes a power source capable of supplying power to the biometrically authorisable device, and a switching arrangement configured to activate the supply of power from the power source to the biometrically authorisable device in response to manipulation of the holder by a user after delivery of the enrolment system, with the holder being arranged such that during the delivery of the enrolment system the supply of power from the power source to the biometrically authorisable device is deactivated;

wherein the enrolment system is arranged to enable an enrolment mode of the biometrically authorisable device after activation of the supply of power from the power source in the holder to the biometrically authorisable device in response to manipulation of the holder by the user, with the enrolment mode of the biometrically authorisable device including an enrolment process in which the user's biometric data can be enrolled to the biometrically authorisable device using the biometric sensor of the biometrically authorisable device; and wherein the enrolment system is configured to use the power from the power source to power the biometrically authorisable device during the enrolment process.

The enrolment system may be configured to carry out the method of the first aspect and may optionally include any of the further features discussed above in connection with that method. Thus, for example, the holder may be a folded card or a box with a slide, as discussed above.

The reference to mail delivery should be understood to include any suitable system for delivery of physical items, such as postal services, courier services and so on, and hence the enrolment system should be suitable for delivery by such systems, for example in terms of its physical size. The enrolment system may be self-contained in that it will enable enrolment of biometric data without the need for interaction with any external system or network. The enrolment system may comprise a suitable outer package to protect the holder and the biometrically authorised device during the delivery to the user. In the case of a biometrically authorisable device with a flat shape, such as a smartcard, then the package may be an envelope and hence would be readily delivered to the user by all mail delivery systems that can deliver letters and similar items.

The switching arrangement may include a physical switch for completing an electrical circuit. As noted above, the holder may be similar to so-called "singing gift cards" and may use a switching arrangement known from such devices, in which case the manipulation of the holder may include opening a folded card. Other manipulations may be used, such as pulling a tab or pressing a button. In some cases it will be appreciated that the manipulation may be a natural movement that the user will carry out, such as opening a folded card. The holder may include printed instructions to the user to prompt the user to carry out the required manipulation. For example, written or diagrammatic instructions may be included on the holder. The holder may also provide the user with instructions for how to carry out the biometric enrolment following activation of the power supply from the power source. For example, these instructions may be written or diagrammatic instructions printed on the holder and/or the holder may include a powered interface for providing instructions, such as a speaker for providing audible instructions or a graphical user interface for providing visible instructions.

The biometrically authorisable device may be a smartcard. The smartcard may be any one of: an access card, a credit card, a debit card, a pre-pay card, a loyalty card, an identity card, or the like. The smartcard optionally has a width of between 85.47 mm and 85.72 mm, and a height of between 53.92 mm and 54.03 mm. The smartcard may have a thickness less than 0.84 mm, and optionally of about 0.76 mm (e.g. ±0.08 mm). More generally, the smartcard may comply with ISO 7816, which is the specification for a smartcard.

Other biometrically authorisable devices may also use the enrolment method, such as wearables and devices used in the context of interactions via the Internet of Things, especially small portable devices. Thus, the enrolment system may comprise one of these devices.

The biometrically authorisable device may be capable of wireless communication, such as using RFID or NFC communication. Alternatively or additionally the biometrically authorisable device may comprise a contact connection, for example via a contact pad or the like such as those used for "chip and pin" cards. In various embodiments, the biometrically authorisable device may permit both wireless communication and contact communication. It will be appreciated that the biometrically authorisable device may have electrical contacts for receiving power from the power source on the holder, and in that case the electrical contacts for receiving power may also act as contact connections for communication purposes.

The biometric sensor may be a fingerprint sensor, which is preferably embedded into the biometrically authorisable device. With this feature the authorised user may initially enroll their fingerprint onto the biometrically authorisable device, and may then be required to place their finger or thumb on the fingerprint sensor in order to authorise some or all uses of the biometrically authorisable device. The processor may include a fingerprint matching algorithm for identifying a fingerprint match between an enrolled user and a fingerprint sensed by the fingerprint sensor.

The enrolment system may be configured such that the enrolment mode of the biometrically authorisable device may be enabled out upon activation of the power supply without any added step. Thus, biometric enrolment may be permitted automatically after a simple physical manipulation of the holder and without added authentication of the user. In this case the biometrically authorisable device may be arranged to require a later authorisation step via an external system before activation of some or all of the secure feature(s) of the device, such as payment functions for a payment smartcard. Thus, the processor may require this added step along with biometric identification in relation to access to the secure feature(s). Possible later authorisation steps via an external system can be as discussed above.

Alternatively, the enrolment system may be arranged to require added authentication to confirm the identity of the user before the enrolment mode is enabled. The enrolment system may be arranged to require the use of both of added authentication by the enrolment system as well as a later authorisation step via an external system.

In the case where the enrolment system requires added authentication to confirm the identity of the user before the enrolment mode is enabled then this may make use of an interface on the holder and/or of an interface on the biometrically authorisable device. As set out above, the interface on the biometrically authorisable device may be the biometric sensor. Another possibility is for an interface to be included on the holder, such as a PIN pad or other interface allowing a code to be entered. The holder may be arranged to activate the enrolment mode of the biometrically authorisable device upon entry of the correct code by the user. The biometrically authorisable device may optionally also use the authorisation via this code to activate access to some or all of the secure feature(s) of the device.

The interaction between the holder and the biometrically authorisable device may involve physical mounting of the biometrically authorisable device to the holder, such as mounting within a suitable recess. Thus the holder may include a recess for receiving the biometrically authorisable device. The recess may resiliently grip the biometrically authorisable device, such as via a friction fit and/or with elastically deformable elements. This can allow for the biometrically authorisable device to be securely held by the holder during delivery and enrolment, but then easily removed by hand by the user once the enrolment process has been completed. The mounting of the biometrically authorisable device to the holder may include an electrical connection for forming an electrical circuit with the biometrically authorisable device and the power source of the holder. Thus, the biometrically authorisable device should not need to be moved or reconfigured relative to the holder in order to activate the supply of power. Instead the required electrical connection should already be in place when the enrolment system is delivered to the user, with activation of the power supply being reliant on manipulation of the holder without relative movement of the holder and the biometrically authorisable device.

The interaction between the holder and the biometrically authorisable device may be limited to the supply of power, such that the holder includes a simple power supply circuit that has a switching function via the switching arrangement and has no other function. Alternatively the holder may itself be a 'smart' device and there may be communication of data between the holder and the biometrically authorisable device in addition to power. Data may be transferred between the holder and the biometrically authorisable device via wired or wireless communication protocols. In the case of wired communication of data this may use the same electrical connections as the power supply. As noted above, the biometrically authorisable device may comprise a contact connection, for example via a contact pad or the like such as those used for "chip and pin" smartcards, and this contact pad may be used for both a power supply from the holder to the biometrically authorisable device and for communication of data. In the case of wireless communication of data this may use a wireless communication system provided on the biometrically authorisable device for other purposes, such as an RFID communication interface provided for RFID communications during normal use of the biometrically authorisable device. Where the biometrically authorisable device is a smartcard then an RFID antenna is often included, such as for contactless communication for a payment smartcard or a transport system smartcard.

Where the biometrically authorisable device and the holder are in communication with each other for transfer of data then the holder may include a processor controlling the data transfer and/or controlling operations of the holder in reaction to data transfer. The holder may provide the biometrically authorisable device with an unlock signal in the case of added authentication via PIN entry or the like on the holder. The holder and the biometrically authorisable device may use public key interchange for added security. The holder may be arranged to prompt certain modes of operation of the biometrically authorisable device in conjunction with the enrolment mode, such as causing LEDs to light up or causing a display on the biometrically authorisable device to show certain information to the user. In the latter case the biometrically authorisable device may include a GUI such as an LED or LCD display or the like.

In relation to either the method or the system referred to above then the enrolment system may include further features as set out below.

As noted above, the use of an added authentication via an interface on the biometrically authorisable device may include an interaction with a fingerprint sensor in a way that differs from standard fingerprint input.

Thus, with the fingerprint authorisable device of this aspect it is possible for users that are unable to enroll for fingerprint authorisation to still use some or all of the features of the device by means of the non-fingerprint authorisation. The user may be provided with a suitable instruction defining non-fingerprint authorisation in the form of a pattern or sequence of actions that the fingerprint sensor can detect in order to confirm that the user is authorised. The fingerprint sensor is used for part of or all of the non-fingerprint authorisation process, meaning that the proposed non-fingerprint authorisation can be carried out with no requirement for adding further sensors to the device, although if other sensors are present, such as an accelerometer for example then these may also be utilised.

The action(s) detected via the fingerprint sensor may include one or more of a stationary contact with the sensor, a moving contact with the sensor, a time period of contact with the sensor, a direction of movement of contact with the sensor, a number of contacts with the sensor, or a time period where there is no contact with the sensor (i.e. a time period between contacts). Preferably the non-fingerprint authorisation requires a combination of different actions, which may include a sequence of actions on the fingerprint sensor and/or at least one action on the fingerprint sensor in combination with at least one action via another input or sensor.

The contact may be any contact detectable via the fingerprint sensor of the device. The nature of fingerprint sensors means that they are arranged to identify contact with the skin and so the contact may be a contact of the skin, for example contact with a fingertip or thumbtip. The interactions with the fingerprint sensor that are used during the non-fingerprint authorisation may be distinguished from interactions during fingerprint authorisation by the fact that the fingerprint sensor is not used to gather a sufficient level of information about the contact to enable a fingerprint authorisation.

An action in the form of stationary contact detected by the fingerprint sensor may include a detection of the presence of a contact, as distinct from the absence of a contact.

An action in the form of a moving contact detected by the fingerprint sensor may include a detection of the direction of movement and/or a speed of the movement. The direction may be identified relative to one or more axes of the device. For example in the case of a smartcard the processor may be arranged to distinguish between a contact moving parallel with the long side of the card and a contact moving parallel with the short side of the card. The action(s) may include a sequence with parallel and/or perpendicular movements, or more complex movements defined by the user, such as a rotating contact or a circular movement.

Whether the fingerprint sensor is used to simply detect the presence of a contact or to detect more complex characteristics the actions detected by the fingerprint sensor may include a time period of one or more contacts, a number of contacts and/or the spacing in between contacts, similar to codes such as Morse code, for example. The interaction with the device required for the non-fingerprint authorisation may hence include or consist of a code input by a sequence of stationary or moving contacts with the sensor.

The non-fingerprint authorisation may alternatively or additionally include one or more of the following:
- masking a part of the sensor with or without a fingerprint being applied to the sensor, for example covering a certain corner of the sensor;
- placement of two digits on the sensor so that the sensor sees side-by-side fingerprints with a gap or junction between them;
- tapping or swiping the sensor or parts of the sensor in a preset sequence;
- covering the sensor with a digit or otherwise for a certain amount of time; and/or
- other interactions with the fingerprint sensor.

The secure feature(s) of the biometrically authorisable device may for example include authorisation of a transaction for a bank card, access to data stored on the card, entry to a secure area via an access card and so on.

The biometrically authorisable device may comprise an accelerometer for sensing movements of the biometrically authorisable device and the processor may use movements sensed by the accelerometer as a part of or all of an added authentication step. Thus, the user may be instructed to input a code via movement of the biometrically authorisable device in order to confirm their identity or to activate the secure feature(s) of the biometrically authorisable device. This may require the user to physically interact with the smartcard in a certain way, such as by tapping the smartcard on a hard surface.

The accelerometer may also allow for control of the biometrically authorisable device based on movements sensed by the accelerometer. For example, movements sensed by the accelerometer may be used to activate various operating modes of the biometrically authorisable device. Advantageously the smartcard is a contactless smartcard and thus the user can switch between different modes with the only contact being holding of the card by the user. This can allow for increased features and increased complexity in how the smartcard is used, without detriment to the ease of operation of the card.

The processor may be arranged to identify the movements of the biometrically authorisable device based on the output of the accelerometer, and to change the operating mode of the biometrically authorisable device or determine that a user is authorised in response to pre-set movements. The pre-set movements may include any or all or translations, rotations, acceleration, jerk/impulse and so on. In addition, the processor may determine the length of a time period without motion, i.e. a time period indicative of no active usage of the biometrically authorisable device, and this may also be used to change the operating mode of the biometrically authorisable device and/or to deactivate features, such as a secure feature, that are currently activated. The processor may also be arranged to identify repeated movements or sequences of movements, such as a double tap, or a translational movement followed by a rotation such as a sliding and twisting motion.

Although movements can be detected by an accelerometer with a single sensing axis, it is preferred to be able to detect accelerations in all directions. This may be done via multiple accelerometers, but preferably a single accelerometer is used that can detect acceleration in all directions, such as a tri-axis accelerometer.

The accelerometer may be a micro-machined accelerometer such as a MEMS accelerometer. Alternatively a piezoelectric sensor may be used, such as a dedicated piezoelectric accelerometer or another piezoelectric sensor that can sense accelerations (e.g. a piezoelectric sounder or microphone). The use of these types of devices allows for them to be installed on a smartcard without the need for increasing the size of the smartcard. They also have low power consumption, which can be a design restriction for smartcards as set out above. Piezoelectric sensors may advantageously be incorporated into the device in such a way that there is zero power consumption until an input is detected by the piezoelectric sensor. The accelerometer may use a sense element such as a micro-machined cantilever or seismic mass. In an example implementation the acceleration sensing is based on the principle of a differential capacitance arising from acceleration-induced motion of the sense element. A possible accelerometer that could be used is a Tri-axis Digital Accelerometer such as those provided by Kionix, Inc. of Ithaca, New York, USA. An example embodiment uses the Kionix KXCJB-1041 accelerometer. The processor of the biometrically authorisable device may be arranged to control the enrolment of biometric data via the biometric sensor.

Where a processor is referred to herein it should be understood that this may include multiple processors working together. For example, the biometric sensor and/or the accelerometer (if present) may each be provided with a dedicated processor that interacts with a main processor that has control of other features of the smartcard. Moreover, whilst in the preferred embodiment it is said that there is a processor that controls communications with the biometrically authorisable device as well as a fingerprint processor that is a part of the fingerprint authentication engine, it should be appreciated that these two processors may be each made up of multiple processors or could be separate software modules of a single combined processor.

After the enrolment process then the biometrically authorisable device may typically require the user to identify themselves via the biometric sensor in order to authorise some or all uses of the device. In the case of a fingerprint sensor then a fingerprint matching algorithm may be used by the processor to identify a fingerprint match between an enrolled user and a fingerprint sensed by the fingerprint sensor.

It is preferred for the device to be arranged so that it is impossible to extract the data used for identifying users. The transmission of this type of data outside of the device is considered to be a big risk to the security of the device.

Hence, the enrolment may be fully self-contained with the enrolment process only requiring access to the enrolment system and with the enrolled biometric data not being communicated outside of the biometrically authorisable device.

In accordance with the proposed device, both the matching and enrolment scans may be performed using the same biometric sensor. As a result, scanning errors can be balanced out because, for example, if a user tends to present their finger to a fingerprint sensor with a lateral bias during enrolment, then they are likely to do so also during matching with the same sensor.

The first enrolled user of the biometrically authorisable device may be provided with the ability to later prompt an enrolment mode for subsequent users to be added. Alternatively or additionally it may be possible to prompt the enrolment mode of the control system via outside means, such as via interaction between the biometrically authorisable device and a secure system, which may be a secure system controlled by the manufacturer or by another authorised entity.

The biometrically authorisable device may be a portable device, by which is meant a device designed for being carried by a person, preferably a device small and light enough to be carried conveniently. The biometrically authorisable device can be arranged to be carried within a pocket, handbag or purse, for example. As noted above, the biometrically authorisable device may be a smartcard such as a fingerprint authorisable RFID card. The device may be a control token for controlling access to a system external to the control token, such as a one-time-password device for access to a computer system or a fob for a vehicle keyless entry system. The biometrically authorisable device is preferably also portable in the sense that it does not rely on a wired power source. The biometrically authorisable device may be powered by an internal battery and/or by power harvested contactlessly from a reader or the like, for example from an RFID reader.

The biometrically authorisable device may be a single-purpose device, i.e. a device for interacting with a single external system or network or for interacting with a single type of external system or network, wherein the device does not have any other purpose. Thus, the device is to be distinguished from complex and multi-function devices such as smartphones and the like.

Certain preferred embodiments of the present invention will now be described in greater detail, by way of example only and with reference to the accompanying drawings, in which.

By way of example the invention is described in the context of a fingerprint authorised smartcard that uses contactless technology and uses power harvested from the reader. These features are envisaged to be advantageous features of a biometrically authorisable device using the proposed enrolment system but are not seen as essential features and hence the biometrically authorisable device may take a different form, such as a being wearable device, a dongle and/or a device for biometrically secured interactions with the "Internet of Things". In the discussion below embodiments of a fingerprint authorised smartcard are first described with reference to FIGS. 1 to 3, and then an enrolment method and the associated enrolment system are then described with reference to FIGS. 4 and 5.

Figure 1:
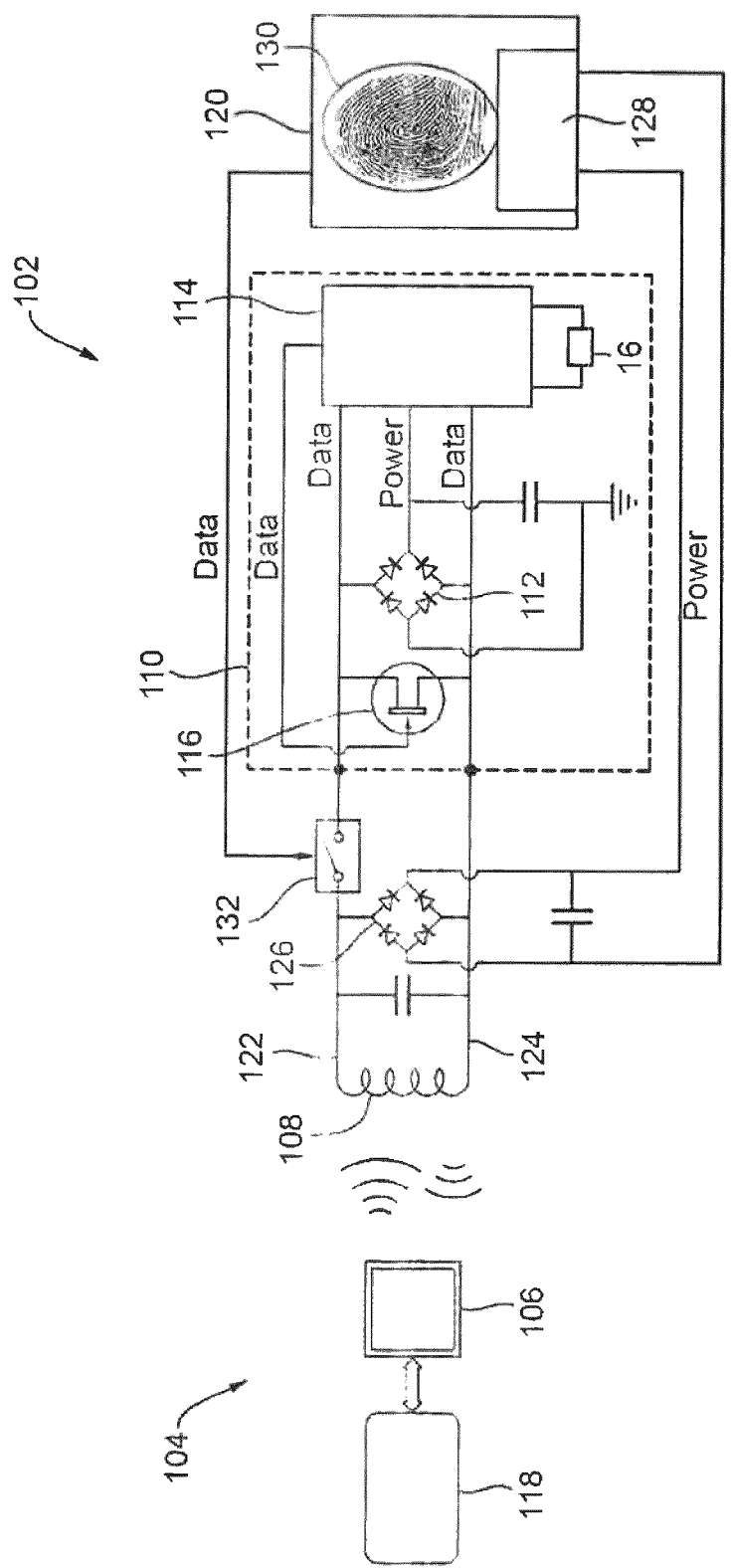
FIG. 1 is a diagram of a circuit for a smartcard incorporating an accelerometer along with a biometric sensor in the form of a fingerprint area sensor.

FIG. 1 shows the architecture of a smartcard 102. A powered card reader 104 transmits a signal via an antenna 106. The signal is typically 13.56 MHz for MIFARE® and DESFire® systems, manufactured by NXP Semiconductors, but may be 125 kHz for lower frequency PROX® products, manufactured by HID Global Corp. This signal is received by an antenna 108 of the smartcard 102, comprising a tuned coil and capacitor, and then passed to a communication chip 110. The received signal is rectified by a bridge rectifier 112, and the DC output of the rectifier 112 is provided to processor 114 that controls the messaging from the communication chip 110.

A control signal output from the processor 114 controls a field effect transistor 116 that is connected across the antenna 108. By switching on and off the transistor 116, a signal can be transmitted by the smartcard 102 and decoded by suitable control circuits 118 in the reader 104. This type of signalling is known as backscatter modulation and is characterised by the fact that the reader 104 is used to power the return message to itself.

An accelerometer 16, where present, is connected in an appropriate way to the processor 114. The accelerometer 16 can be a Tri-axis Digital Accelerometer as provided by Kionix, Inc. of Ithaca, New York, USA and in this example it is the Kionix KXCJB-1041 accelerometer. The accelerometer 16 senses movements of the card and provides an output signal to the processor 114, which is arranged to detect and identify movements that are associated with required operating modes on the card as discussed below. The accelerometer 16 can also be used in an authentication process linked with enrolment of biometric (fingerprint) data as discussed below.

A fingerprint authentication engine 120 is connected to the processor 114 in order to allow for biometric authentication of the user based on a finger or thumb print. The fingerprint authentication engine 120 can be powered by the antenna 108 so that the card is a fully passive smartcard 102. In that case the fingerprint identification of an authorised user is only possible whilst power is being harvested from the card reader 104 or with power from an outside source with a wired connection to the smartcard 102.

As used herein, the term "passive smartcard" should be understood to mean a smartcard 102 in which the communication chip 110 is powered only by energy harvested from an excitation field, for example generated by the card reader 118. That is to say, a passive smartcard 102 relies on the reader 118 to supply its power for broadcasting. A passive smartcard 102 would not normally include a battery, although a battery may be included to power auxiliary components of the circuit (but not to broadcast); such devices are often referred to as "semi-passive devices".

Similarly, the term "passive fingerprint/biometric authentication engine" should be understood to mean a fingerprint/biometric authentication engine that is powered only by energy harvested from an excitation field, for example the RF excitation field generated by the card reader 118.

It should be noted that in alternative embodiments battery powered and hence non-passive smartcards may be provided and may have the same features in relation to the accelerometer, fingerprint sensor, enrolment process, and so on. With these alternatives the smartcard can have the same features aside from that the use of harvested power may be replaced by the power from a battery that is contained within the card body.

Figure 2:
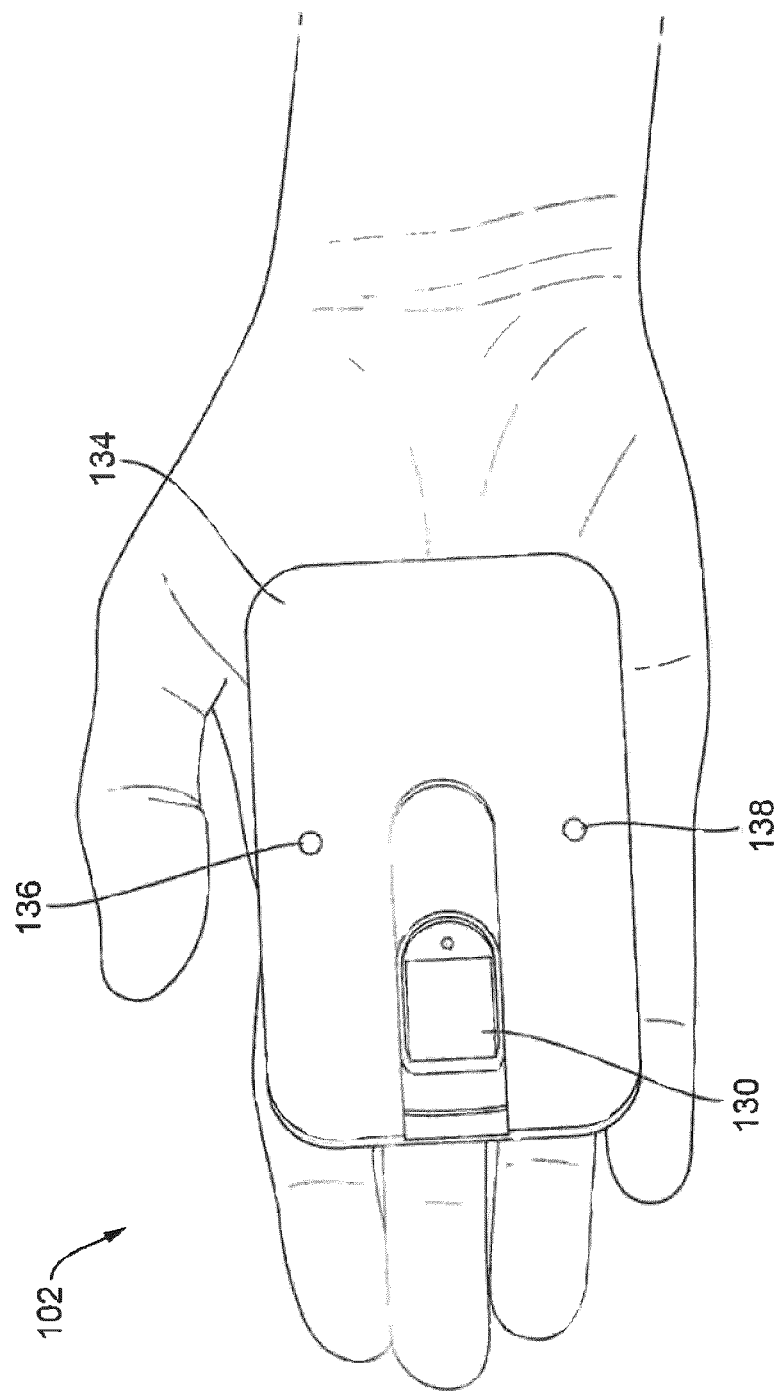
FIG. 2 illustrates a smartcard with an external housing.
Figure 3:
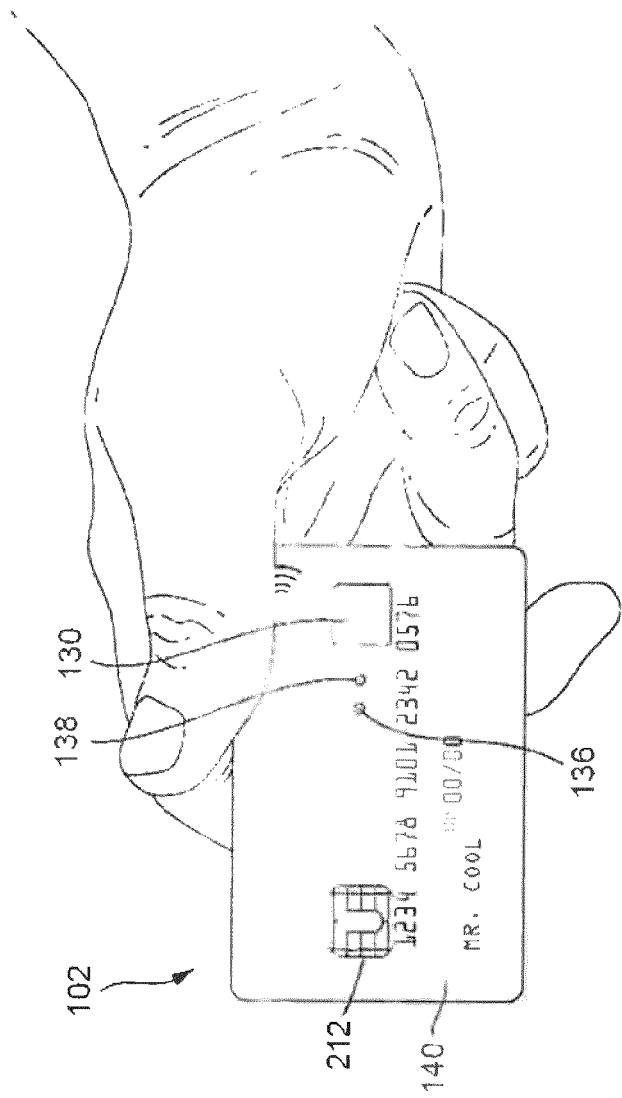
FIG. 3 shows an example laminated type smartcard

The card body can be a card housing 134 as shown in FIG. 2 or a laminated card body 140 as shown in FIG. 3. It will be appreciated that there are significant constraints on the size of the smartcard 102.

The antenna 108 comprises a tuned circuit including an induction coil and a capacitor, which are tuned to receive an RF signal from the card reader 104. When exposed to the excitation field generated by the reader 104, a voltage is induced across the antenna 108.

The antenna 108 has first and second end output lines 122, 124, one at each end of the antenna 108. The output lines of the antenna 108 are connected to the fingerprint authentication engine 120 to provide power to the fingerprint authentication engine 120. In this arrangement, a rectifier 126 is provided to rectify the AC voltage received by the antenna 108. The rectified DC voltage is smoothed using a smoothing capacitor and supplied to the fingerprint authentication engine 120.

The fingerprint authentication engine 120 includes a fingerprint processor 128 and a fingerprint reader 130, which can be an area fingerprint reader 130, mounted on a card housing 134 as shown in FIG. 2 or fitted so as to be exposed from a laminated card body 140 as shown in FIG. 3. The card housing 134 or the laminated body 140 encases all of the components of FIG. 1, and is sized similarly to conventional smartcards. The fingerprint authentication engine 120 can be passive and hence powered only by the voltage output from the antenna 108, or there may be battery power as mentioned above. The fingerprint processor 128 comprises a microprocessor that is chosen to be of very low power and very high speed, so as to be able to perform biometric matching in a reasonable time.

The fingerprint authentication engine 120 is arranged to scan a finger or thumb presented to the fingerprint reader 130 and to compare the scanned fingerprint of the finger or thumb to pre-stored fingerprint data using the fingerprint processor 128. A determination is then made as to whether the scanned fingerprint matches the pre-stored fingerprint data. The time required for capturing a fingerprint image and authenticating the bearer of the card 102 may be less than one second.

If a biometric match is determined then the processor 114 takes appropriate action depending on its programming. In this example full access to secure features of the smartcard (e.g. payment functions) requires a biometric authorisation (embodied by the fingerprint authorisation in this example). If there is a match with enrolled biometric data then the processor 114 permits use of the smartcard 102 with the contactless card reader 104. Thus, the communication chip 110 is only authorised to transmit a signal to the card reader 104 when the multifactor authentication process is satisfied. The communication chip 110 transmits the signal by backscatter modulation.

Where an accelerometer 16 is used the processor 114 receives the output from the accelerometer 16 and this allows the processor 114 to determine what movements of the smartcard 102 have been made. The processor 114 may identify pre-set movements that are linked with required changes to the operating mode of the smartcard 102. As discussed above, the movements may include any type of or combination of rotation, translation, acceleration, jerk, impulse and other movements detectable by the accelerometer 16.

The operating modes that the processor 114 activates or switches to in response to an identified movement associated with the require change in operating mode may include any mode of operation as discussed above, including turning the card on or off, activating secure aspects of the card 102 such as contactless payment and/or communications with the card reader 104, or changing the basic functionality of the card 102 for example by switching between operating as an access card, a payment card, a transportation smartcard, switching between different accounts of the same type (e.g. two bank accounts), switching between communications protocols (such as blue tooth, Wifi, NFC) and/or activating a communication protocol, activating a display such as an LCD or LED display, obtaining an output from the smartcard 102, such as a one-time-password or the like, or prompting the card 102 to automatically perform a standard operation of the smartcard 102. It will be appreciated that the smartcard 102 can readily be programmed with any required characteristics in terms of the action taken in reaction to events detected by the accelerometer 16.

The processor 114 has a learn mode to allow for the user to specify which movements (including combinations of movements) should activate particular operating modes. In the learn mode the processor 114 prompts the user to make the desired sequence of movements, and to repeat the movements for a predetermined set of times. These movements are then allocated to the required operating mode. The processor 114 can implement a dropped card mode and/or a biometric failure back up mode as discussed above.

In some circumstances, the owner of the biometric smartcard 102 may suffer an injury resulting in damage to the finger that has been enrolled on the card 102. This damage might, for example, be a scar on the part of the finger that is being evaluated.

Such damage can mean that the owner will not be authorised by the card 102 since a fingerprint match is not made. In this event the processor 114 may prompt the user for a back-up identification/authorisation check via a sequence of movements. The user can hence have a "password" entered using movements of the card to be used in the event that the biometric authorisation fails.

After such a back-up authorisation the card 102 could be arranged to be used as normal, or it could be provided with a degraded mode in which fewer operating modes or fewer features of the cards 102 are enabled. For example, if the smartcard 102 can act as a bank card then the back-up authorisation might allow for transactions with a maximum spending limit lower than the usual maximum limit for the card.

Figure 4:
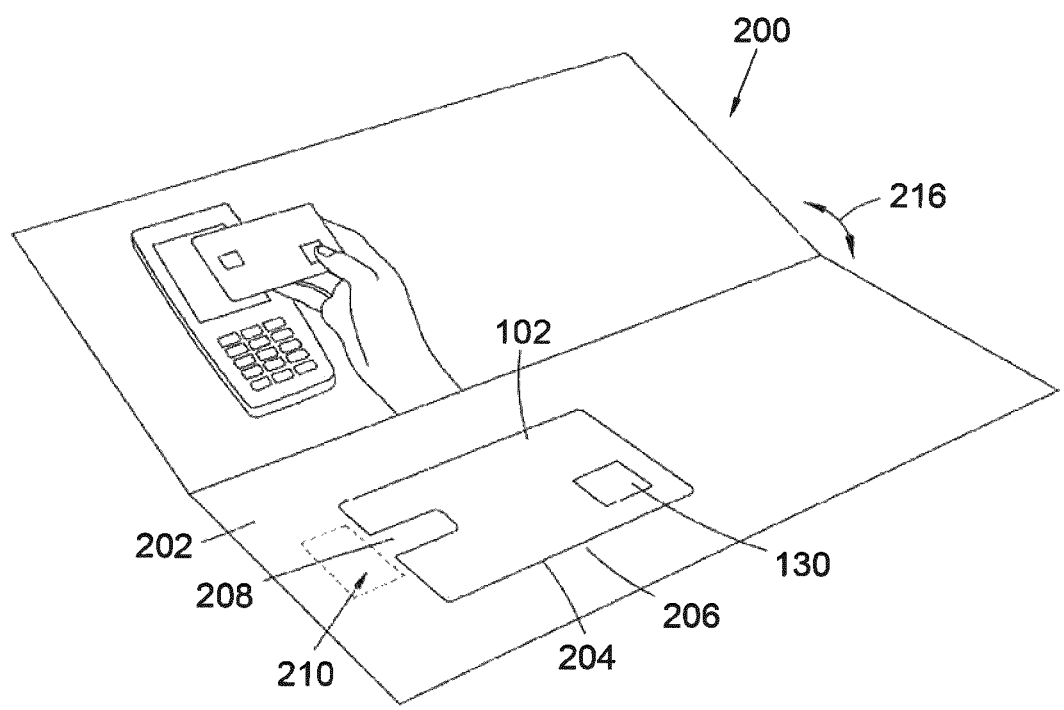
FIG. 4 is an example of an enrolment system with a smartcard and an associated holder.
Figure 5:
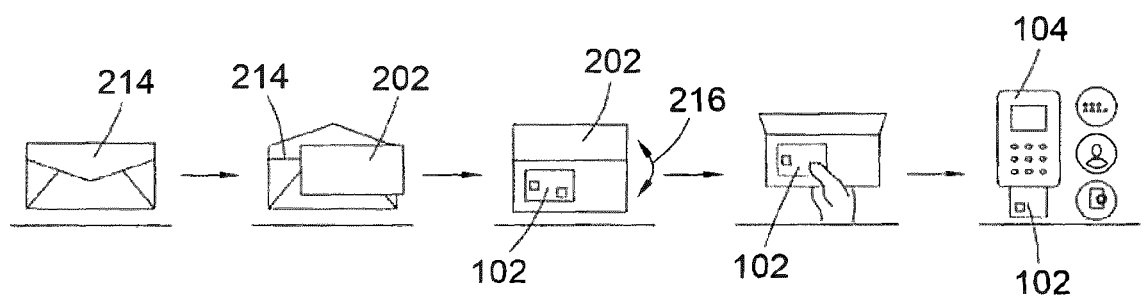
FIG. 5 is a schematic illustration of a sequence of steps for enrolment using the enrolment system of FIG. 4.

Turning now to the disclosure of FIGS. 4 and 5, it will be understood that these show an enrolment system 200 that can be used for biometric enrolment of the smartcards 102 of FIG. 2 or FIG. 3, as well as further other biometrically authorisable devices.

The enrolment system 200 is for biometric enrolment of the smartcard and hence in this example it is used during enrolment of fingerprint data via the fingerprint sensor 130 of the smartcard 102. The enrolment system 200 includes the smartcard 102 mounted to a holder 202. In this example the holder 202 is a folded card shape, similar to a gift card, with a recess 204 for holding the smartcard 102. The recess 204 includes cut-outs 206 for enabling easier removal of the smartcard 102, which is held in the recess mainly by friction fit. A tab 208 extends inward over the top of the smartcard 102 in the recess 204 in order to allow for electrical contact to be made between a power supply system 210 on the holder and contact pads 212 on the smartcard 102. The contact pads 212 are not visible in FIG. 4 since they are beneath the tab 208, but then can be seen in relation to a laminated smartcard 102 in FIG. 3. The enrolment system 200 including the biometrically authorisable device and the holder is arranged to be delivered to an end user by a mail delivery service, and in this case it is clear to see that it can be delivered by postal service or courier service and so on since it is of the same shape and size as a typical letter. For delivery purposes the holder 202 and the smartcard 102 mounted within it would be placed in an envelope 214, as shown in FIG. 5

The holder 202 includes the power supply system 210, which is provided with a power source capable of supplying power to the smartcard during an enrolment process. The power source may for example be a button cell (watch battery) with a suitably thin profile. The power supply system 210 further includes a switching arrangement configured to activate the supply of power from the power source to the smartcard 102 in response to manipulation of the holder by a user after delivery of the enrolment system. In this case the manipulation of the holder 202 takes the form of opening of the folded card as illustrated by the arrow 216. Opening the card may for example move an internal slider and complete an electrical circuit to activate the supply of power to the smartcard 102. When the holder is in the mail then it is in the closed configuration and hence the supply of power from the power source to the smartcard is deactivated.

In an alternative arrangement for the holder 202 it takes the form of a box with an internal slider holding the smartcard 102. In that case the holder 202 may include a tab which, when pulled by a user, reveals the smartcard 102 from inside of the box. The smartcard 102 and/or enrolment system can be attached to the slider and the slider may be configured to appear from inside of the box (e.g. by sliding out of an opening of the box) when the tab is pulled. The power source can be housed inside the box and optionally may be on the slider. Movement of the slider is used to complete an electrical circuit to activate the supply of power to the smartcard 102.

The enrolment system 200 enables an enrolment mode of the smartcard 102 after activation of the supply of power from the power source in the holder 202, with the enrolment mode using the power from the power source to power the smartcard 102 during the enrolment process. The enrolment mode can be enabled simply by powering up the smartcard 102 via the power supply 210. In that case it is preferred to further protect the secure feature(s) of the smartcard 102 (e.g. payment functions) by requiring a further authorisation step before access to all the secure features is enabled. This may be similar to card activation for existing bank cards and hence may involve the use of online banking, an app, a telephone call to the card issuer and/or use of a PIN at a card reader such as an ATM or point of sale device.

Alternatively or additionally, the enrolment system 200 may be arranged to require added authentication to confirm the identity of the user before the enrolment mode is enabled. This optional feature may make use of an interface on the holder 202 and/or of an interface on the smartcard 102. The interface on the smartcard 102 may be the fingerprint sensor 130 and this can be used to detect a 'pattern' in interaction of the user with the sensor 130 as discussed above. Another possibility is for an interface to be included on the holder, such as a PIN pad or other interface allowing a code to be entered.

The interaction between the holder 202 and the smartcard 102 may be limited to the supply of power, such that the holder 202 includes a simple power supply circuit 210 that has a switching function via the switching arrangement and has no other function. Alternatively the holder 202 may itself be a 'smart' device and there may be communication of data between the holder 202 and the smartcard via wired or wireless communication protocols.

As shown in FIG. 5 a typical enrolment process for a payment card will hence include receipt of the enrolment system 200 sealed in an envelope 214, opening of the envelope 214 with removal of the holder 202 with the smartcard 102 attached within it. By way of example the holder 202 is shown in FIG. 5 as the folded card holder 202 of FIG. 4. Opening of the holder 202 as shown by the arrow 216, which then activates the enrolment mode for the smartcard 102, enrolment by the user via the sensor 130 on the smartcard 102, and then subsequent activation of the payment functions of the smartcard 102 via PIN entry or contact with the issuer using computer, smartphone app or voicecall.

We claim:

1. A method for biometric enrolment of a biometrically authorisable device, wherein the biometrically authorisable device comprises a biometric sensor for identification of an authorised user and a processor capable of permitting access to one or more secure feature(s) of the biometrically authorisable device based on authentication of the user's identity via the biometric sensor, and wherein the method comprises:
   mounting the biometrically authorisable device to a holder in order to form an enrolment system, wherein the enrolment system including the biometrically authorisable device and the holder is arranged to be delivered to the end user by a mail delivery service;
   providing the holder with a power source capable of supplying power to the biometrically authorisable device, wherein the holder is arranged such that during the delivery of the enrolment system the supply of power from the power source to the biometrically authorisable device is deactivated, and the holder includes a switching arrangement configured to activate the supply of power from the power source to the biometrically authorisable device in response to manipulation of the holder by a user after delivery of the enrolment system;
   delivering the enrolment system to an end user;
   activating the supply of power from the power source in the holder to the biometrically authorisable device in response to manipulation of the holder by the user;
   enabling an enrolment mode of the biometrically authorisable device in which the user's biometric data can be enrolled to the biometrically authorisable device via an enrolment process using the biometric sensor of the biometrically authorisable device; and
   using the power from the power source to power the biometrically authorisable device during the enrolment process.

2. A method as claimed in claim 1, wherein biometrically authorisable device has no internal power source and instead is arranged to rely on power from external sources including the power from the holder and power harvested from an electric field via an antenna of the device.

3. A method as claimed in claim 1, wherein during the delivery the holder and the biometrically authorisable device are housed within an outer package in the form of an envelope.

4. A method as claimed in claim 1, wherein the switching arrangement includes a physical switch for completing an electrical circuit and hence activating of the power supply.

5. A method as claimed in claim 1, wherein the manipulation of the holder by the user includes an action done upon receipt of a delivery.

6. A method as claimed in claim 5, wherein the holder is a folded card and the manipulation of the holder includes opening the folded card.

7. A method as claimed in claim 1, wherein the biometrically authorisable device is a smartcard with a width of between 85.47 mm and 85.72 mm, a height of between 53.92 mm and 54.03 mm, and a thickness less than 0.84 mm.

8. A method as claimed in claim 1, wherein the enrolment system requires added authentication to confirm the identity of the user before the enrolment mode is enabled, wherein the added authentication is obtained via an interface on the holder and/or an interface on the biometrically authorisable device.

9. A method as claimed in claim 8, wherein the added authentication is obtained via the interface on the biometrically authorisable device, and the interface on the biometrically authorisable device is the biometric sensor.

10. A method as claimed in claim 1, wherein the step of enabling an enrolment mode of the biometrically authorisable device is carried out upon activation of the power supply without added authentication of the user.

11. A method as claimed in claim 1, wherein the biometrically authorisable device requires a later authorisation step via an external system after biometric enrolment and before activation of some or all of the secure feature(s) of the device, such as payment functions for a payment smartcard.

12. A method as claimed in claim 11, wherein the later authorisation step via an external system before activation of some or all of the secure feature(s) of the biometrically authorisable device includes the use of one or more of: an online system, such as online banking for a payment card; an app; a telephone call; or use of the biometrically authorisable device with an authorisation code, such as a PIN.

13. A method as claimed in claim 1, wherein the mounting of the biometrically authorisable device to the holder involves physical mounting of the biometrically authorisable device to the holder within a recess formed in the holder.

14. A method as claimed in claim 1, wherein the mounting of the biometrically authorisable device to the holder includes an electrical connection for forming an electrical circuit with the biometrically authorisable device and the power source of the holder such that during the manipulation of the holder by the user the biometrically authorisable device does not need to be moved or reconfigured relative to the holder in order to activate the supply of power.

15. A method as claimed in claim 1, wherein the biometrically authorisable device is a smartcard held on the holder in a recess with a tab extending over the smartcard, wherein the tab provides an electrical connection to a "chip and pin" contact pad on the smartcard.

16. A method as claimed in claim 1, wherein there is communication of data between the holder and the biometrically authorisable device in addition to transfer of power, with the data being transferred between the holder and the biometrically authorisable device via wired and/or wireless communication protocols.

17. A method as claimed in claim 16, wherein the communication of data includes wired communication of data and this uses the same electrical connections as the power supply from the holder to the biometrically authorisable device.

18. A method as claimed in claim 16, wherein the holder includes a processor for controlling the communication of data and/or for controlling operations of the holder in reaction to data transfer.

19. A method as claimed in claim 16, wherein the holder provides the biometrically authorisable device with an unlock signal in the case of added authentication via PIN entry on the holder, and/or wherein the holder and the biometrically authorisable device use public key interchange for added security.

20. A method as claimed in claim 16, wherein the holder prompts certain modes of operation of the biometrically authorisable device in conjunction with the enrolment mode, for example by causing LEDs to light up or causing a display on the biometrically authorisable device to show information to the user.

21. An enrolment system for biometric enrolment of a biometrically authorisable device, the enrolment system comprising the biometrically authorisable device and a holder for the biometrically authorisable device, wherein the biometrically authorisable device is mounted to the holder, and wherein the enrolment system including the biometrically authorisable device and the holder is arranged to be delivered to an end user by a mail delivery service;

wherein the biometrically authorisable device comprises a biometric sensor for identification of an authorised user and a processor capable of permitting access to one or more secure feature(s) of the biometrically authorisable device based on authentication of the user's identity via the biometric sensor;

wherein the holder includes a power source capable of supplying power to the biometrically authorisable device, and a switching arrangement configured to activate the supply of power from the power source to the biometrically authorisable device in response to manipulation of the holder by a user after delivery of the enrolment system, with the holder being arranged such that during the delivery of the enrolment system the supply of power from the power source to the biometrically authorisable device is deactivated;

wherein the enrolment system is arranged to enable an enrolment mode of the biometrically authorisable device after activation of the supply of power from the power source in the holder to the biometrically authorisable device in response to manipulation of the holder by the user, with the enrolment mode of the biometrically authorisable device including an enrolment process in which the user's biometric data can be enrolled to the biometrically authorisable device using the biometric sensor of the biometrically authorisable device; and wherein the enrolment system is configured to use the power from the power source to power the biometrically authorisable device during the enrolment process.

* * * * *